United States Patent

Sakata et al.

Patent Number: 4,709,022
Date of Patent: Nov. 24, 1987

[54] PHEOPHORBIDE DERIVATIVES AND ALKALINE SALTS THEREOF

[76] Inventors: Isao Sakata, 1766-4 Obirai, Kasaoka City, Okayama Pref.; Susumu Nakajima, 4-4-34 Gojo, Midorigaoka, Asahikawa City, Hokkaido; Koichi Koshimuzi, 85-10 Horensan soinishi cho, Nara City, Nara Pref.; Natsuki Samejima, A-42 Idai Shukusha, 3-3 Nijo, Midorigaoka, Asahikawa City, Hokkaido; Kazumi Inohara, 3-9-7 Mikado cho, Fukuyama City, Hiroshima Pref.; Hiroyuki Takata, 2098 Satomi, Satosho cho, Asakuchi gun, Okayama Pref., all of Japan

[21] Appl. No.: 746,386

[22] Filed: Jun. 19, 1985

[30] Foreign Application Priority Data

Jun. 22, 1984 [JP] Japan .................................. 59-128478

[51] Int. Cl.$^4$ ........................................... C07D 487/22
[52] U.S. Cl. ..................................................... 540/145
[58] Field of Search .................... 260/245.91; 514/410; 540/145

[56] References Cited

FOREIGN PATENT DOCUMENTS 185220 11/1982 Japan .

OTHER PUBLICATIONS

Ellsworth et al, Chemical Abstracts, vol. 88, (1978), 59586r.
Boxer et al, JACS, vol. 98, (1976), pp. 5406–5408.
Cox et al, J. Chem. Soc., (1974), pp. 512–516.
Scheer et al, JACS, vol. 97, No. 11, (1975), pp. 3273–3275.
Wasielewski et al, Tetrahedron Letters, No. 12, (1978), pp. 1043–1046.
McFeeters, Chemical Abstracts, vol. 82, (1975), 134838f.
Scheer et al, Tetrahedron, vol. 28, (1972), pp. 5839–5856.

Primary Examiner—Richard L. Raymond
Attorney, Agent, or Firm—William J. Daniel

[57] ABSTRACT

Pheophorbide derivatives and alkaline salts thereof having the general formula (A):

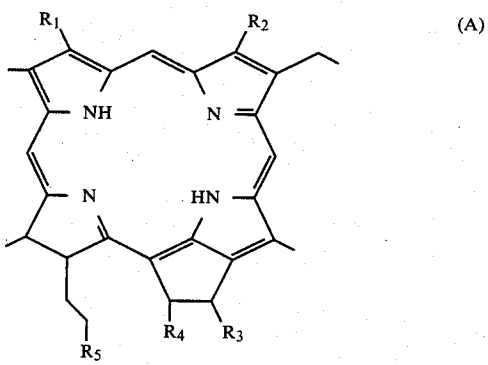

wherein
$R_1$ represents $-CH=CH_2$, $-CH(OH)CH_3$, $-CH(OCH_2CH_2OH)CH_3$ or $-CH(OCOCH_3)CH_3$
$R_2$ represents $-CH_3$, $-CHO$ or $-CH_2OH$
$R_3$ represents $=O$, $-OH$ or $-OCOCH_3$
$R_4$ represents $-H$, $-COOCH_3$, $-COOCH_2CH_2OH$, $-COOCH_2CH_2OCOCH_3$, or a $-CONH-$ containing residue of an amino acid and
$R_5$ represents $-COOH$, $-COONa$ or $-COOCH_3$; provided, however, said derivatives and alkaline salts exclude pheophorbide, 9-desoxo-9-hydroxy-pheophorbide and pyropheophorbide.

Dimeric pheophorbide derivatives and alkaline salts thereof represented by the general formula (B):

(Abstract continued on next page.)

(B) wherein $R_1$ through $R_5$ are the same as in general formula (A), are useful for treating cancer having a strong preferential affinity for cancer cells over normal cells and exerting upon irradiation a destructive effect on such cancer cells.

1 Claim, 7 Drawing Figures

SODIUM 2-DESETHENYL-λ-(†-ACETYLOXY ETHYL)-9-DESOXO-9-ACETYLOXY-PHEOPHORBIDE (IV)

FIG. 1d.

SODIUM ETHYLENE GLYCOL di-10b-PHEOPHORBATE (X)

Figure 1A:
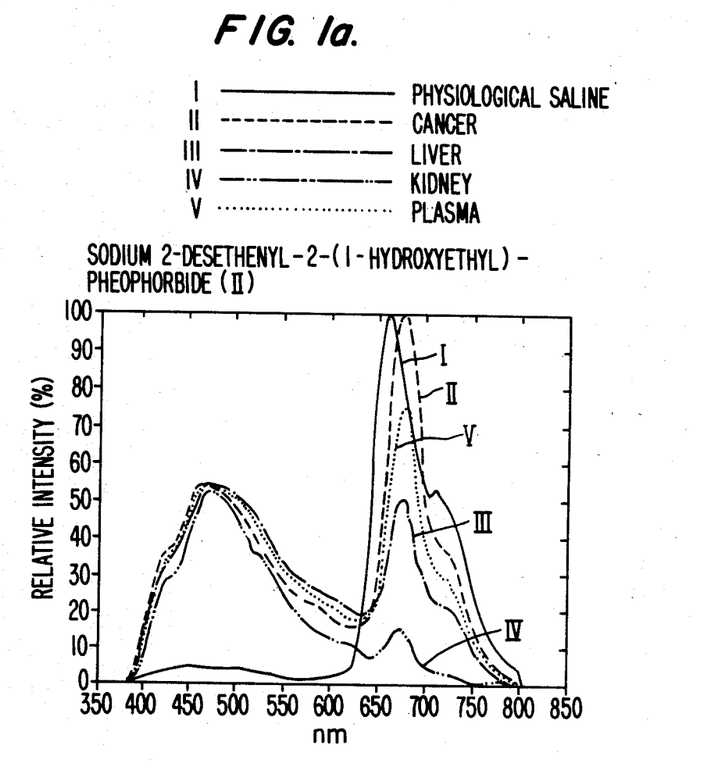
Figure 1B:
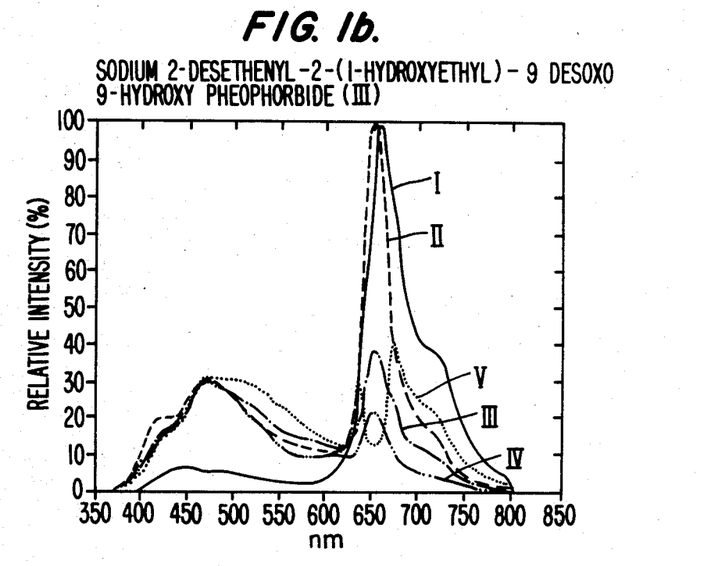
Figure 1C:
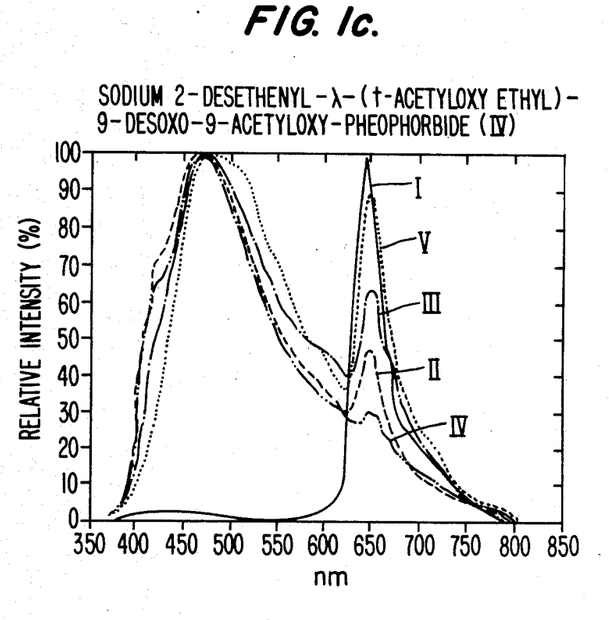
Figure 1D:
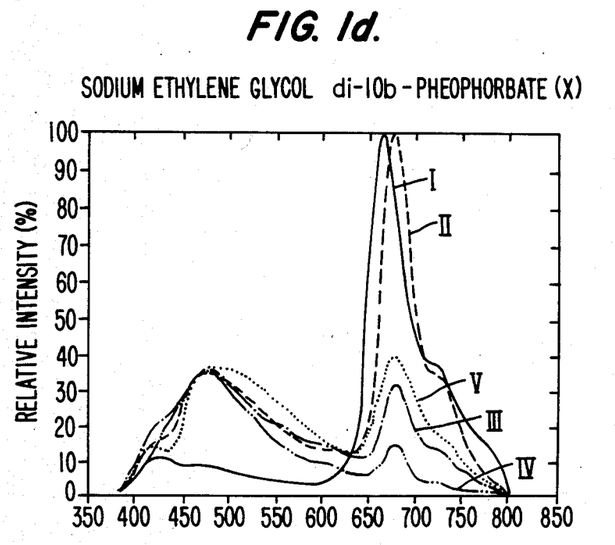
Figure 1E:
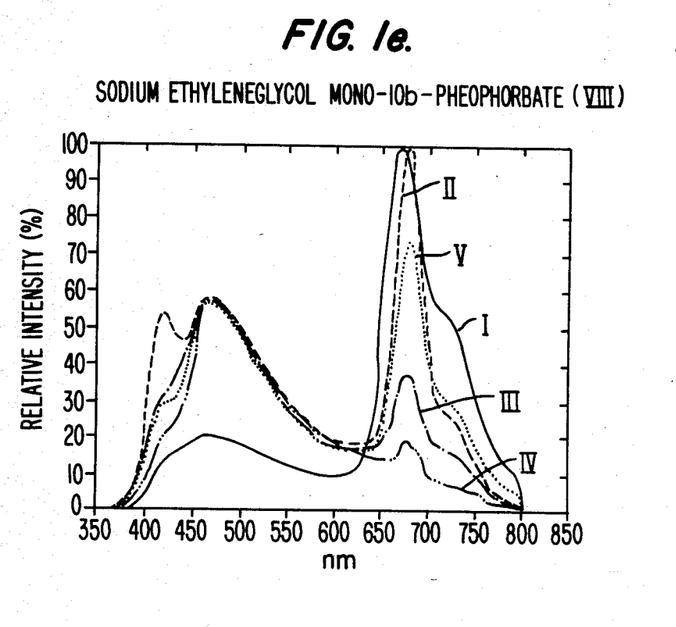

FIG. 1e.
SODIUM ETHYLENEGLYCOL MONO-10b-PHEOPHORBATE (VIII)

Figure 1F:
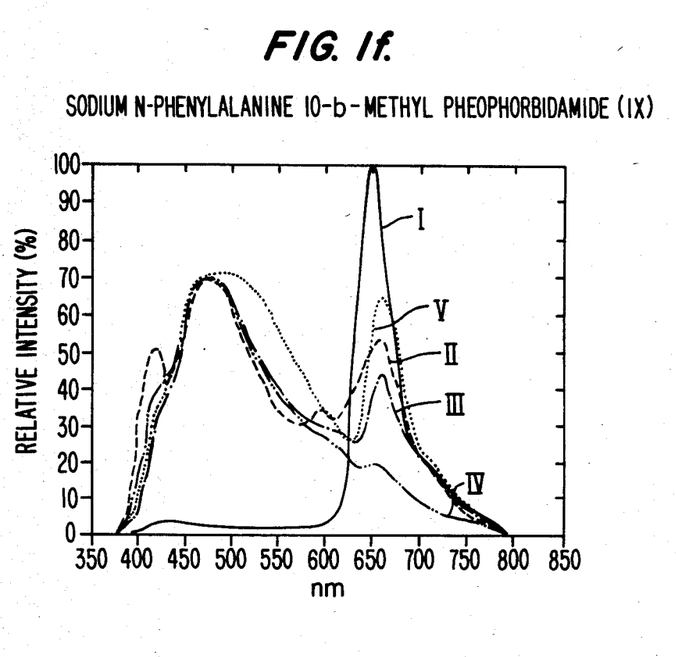

FIG. 1f.
SODIUM N-PHENYLALANINE 10-b-METHYL PHEOPHORBIDAMIDE (IX)

FIG. 2.

PHEOPHORBIDE DERIVATIVES AND ALKALINE SALTS THEREOF

1. FIELD OF THE INVENTION

The present invention relates to a novel photosensitizer for use in cancer treatment comprising a pheophorbice derivative as its active constituent. Compounds according to the present invention are novel, not found in the literature and are useful in cancer treatment by reason of their phramacological effects such as photo-sensitivity and accumulative and destructive effects in cancer cells upon irradiation.

2. BACKGROUND OF THE INVENTION

Porphyrin compounds, particularly porphone derivatives obtained from hemoglobin, are known for their binding property with cancer tissue and photo-dynamic characteristics. Their use in cancer treatment is now being studied. However, production of porphyrin compounds requires animal blood which is limited in supply and needs extensive production steps. Animal blood, moreover, is not readily available as a commodity and phorphone derivatives, such as hematoporphyrine, which are said to be the active constituent of such derivatives are chemically unstable and it is extremely difficult to obtain them with high purity.

The present inventors have long been engaged in the study of chlorophyll related compounds and established a highly economical process for separating pheophorbide using naturally photo-synthesized organisms which are available in a stable and inexpensive supply and is described in Japanese Patent Application Laid-open No. 83-69884.

On the hypothesis that phorbines derived from pheophorbides may include compounds which demonstrate more potent physiological activities than porphines derived from blood, the present inventors continued their study and found for the first time that 9-desoxo-9-hydroxy-pheophorbide derivatives and their alkaline salts which are chemical reduction products of pheophorbide demonstrate highly potent physiological activities on cancer and photosensitivity (Japanese Patent Application No. 198934/83 and corresponding U.S. patent application Ser. No. 664,375).

Upon further studies, the present inventors found that other pheophorbide derivatives having various functional groups and their dimers (hereinafter referred to as the inventive compounds), and falling within the following general formula (A):

wherein $R_1$ represents $-CH=CH_2$, $-CH(OH)CH_3$, $-CH(OCH_2CH_2OH)CH_3$ or $-CH(OCOCH_3)CH_3$

$R_2$ represents $-CH_3$, $-CHO$ or $-CH_2OH$ $R_3$ represents $=O$, $-OH$ or $-OCOCH_3$ $R_4$ represents $-H$, $-COOCH_3$, $-COOCH_2CH_2OH$, $-COOCH_2CH_2OCOCH_3$, or a $-CONH-$ containing residue of an amino acid and $R_5$ represents $-COOH$, $-COONa$ or $-COOCH_3$;

exclusive of pheophorbide, 9-desoxy-9-hydroxy-pheophorbide, and pyropheophorbide, and the following general formula (B):

wherein $R_1$ through $R_5$ are the same as general formula (A) and have excellent pharmacological properties, such as marked affinity to cancerous tissues, high photo-sensitivity and strong destructive effect upon irradiation on cancerous tissue that are superior to those observed with porphine compounds.

It has heretofore been known that porphone derivatives obtained from hemoglobin, i.e., hematoporphyrin and diacetyl hematoporphyrin, are likely to undergo conjugation with cancerous tissues and are photosensitive. Endo et al have recently found that 10-hydroxy-pheophorbide is carcinostatic (Japanese Patent Application Laid-open No. 185220/82). York et al reported on the bactericidal effect on ethylene-diamine hydrochloride of pheophorbide (Japanese Patent Application Laid-open No. 981/83). The latter application relates to an antibacterial agent comprising water soluble phorbine derived from pheophorbide by converting the same into its ethylenediamine hydrochloride salt.

As regards the instant dimers of general formula (B), processes for synthesizing chlorophyll dimers are disclosed in the literature (M. R. Wasielewski et al, C.A. 86, 68532f(1977), C.A. 88 148988r(1978) and S. G. Boxer et al, J.A.C.S., 1976, 5406), but these products are different. Moreover, the aim of these authors was to synthesize the chlorophyll dimers as a part of a study in elucidating the mechanism of photo-synthesis in order to obtain compounds having an UV absorption profile more similar to that of chlorophyll P-700. These references do not discuss the physiological activities of the compounds in question on cancerous tissues which are the main object of the present invention. It has so far been unknown that phorbines had such strong physiological activities.

3. DETAILED DESCRIPTION OF THE INVENTION

The pharmacological activity of the inventive compounds will now be explained. The inventive compounds accumulate selectively in cancer tissues and only slowly excrete therefrom. When irradiated with light, they react and produce singlet oxygen having a strong oxidizing effect to thereby destroy cancer cells. On the other hand, the inventive compounds are readily excreted from normal organs and cells; and, therefore, cancer can be treated by such compounds without damage to normal cells.

As regards their effects on cancer, most porphones, except for a very few substances, show no selective affinity to cancer cells although they are photo-sensitive. Absence of selectively leads when exposed to irradiation to destruction of normal cells as well as cancer cells.

The inventive compounds are of great utility as they are characterized by a combination of all the properties mentioned above (i.e., affinity to cancer cells, photosensitivity, destructive effect upon irradiation on cancer). They can be used not only singly but in combination.

The preparation of the compounds according to the present invention will now be described. Generally, there are two ways of preparing the inventive compounds having the general formula (A). According to one process, pheophobide (designated I) is treated with hydrobromic acid to obtain 2-desethenyl-2-(1-hydroxyethyl)-pheophorbide (designated II), which is then reduced to obtain 2-desethenyl-2-(1-hydroxyethyl)-9-desoxo-9-hydroxy-pheophorbide (designated III). III is acetylated to respectively obtain its diacetylate (IV). These reactions can be expressed by the following chemical equations:

In a practical application of the present invention, I is dissolved in a solution of hydrobromic acid in acetic acid, reacted, and neutralized to obtain II. II is reacted using a suitable reducing agent such as $NaBH_4$ in the same manner as in the process for preparing the prior application substance to obtain the product III. The diacetylated product IV can be obtained from III by reaction with acetic anhydride in solution in pyridine in the usual way.

According to an alternative process for preparing compounds of the general formula A, methylpheophorbide (designated V) is ester-exchanged with ethylene glycol to obtain ethylene glycol mono-10b-methyl pheophorbate (VI), and V is also ester-exchanged with phenylalanine t-butyl ester to obtain N-phenylalanine t-butyl ester 10b-methylpheophorbidamide (VII). VI and VII are subjected to acid hydrolysis to obtain ethylene glycol mono-10b-methyl pheophorbate (VIII) and N-phenylalanine 10b-methyl phoeophorbide (IX), respectively. These reactions can be expressed by the following chemical equations:

Hydroxides, reduction products or acetylates of VIII and IX may also be produced respectively by subjecting the esters of pheophorbide to hydrobromic acid treatment, reduction or acetylation as mentioned above.

In a practical application of the alternative method, V is dissolved in a suitable solvent such as xylene or DMF, ethylene glycol is added and the mixture heated to achieve the reaction to obtain VI. Alternately, phenylalanine tu-butyl ester is added in place of ethylene glycol, heated and reacted to obtain VII. The resultant product VI is mixed with 50% $H_2SO_4$ and the product VII with $CF_3COOH$ and respectively reacted to obtain VIII and IX.

The inventive compounds of general formula (B) are obtained by condensing VIII with I through ester-exchange to obtain ethylene glycol di-10b-pheophorbate (X). The reaction can be expressed by the following equation:

(X)

The phoeophorbide dimer (X) can be subjected to hydrobromic acid treatment, reduction or acetylation in the same manner as mentioned above to produce hydroxides, reduction products or acetylates of X, respectively.

In a practical application of the latter procedure, VIII may be dissolved in a suitable solvent such as DMF or DMA, mixed with I, heated and reacted to obtain X.

As a still another way of preparing the invention substances, it is possible to form the hydroxide or reduction product of methyl phoeophorbide (V) prior to condensation by ester-exchange, and obtain preferred results. Any combination of reactions other than those mentioned above may also be employed so long as they include hydroxidize-formation, hydrolysis and ester-exchange reactions. It is also preferable but not essential to add a suitable antioxidant or solvent and heat the reaction system. Although pheophorbide is used as the starting material, pheophorbide, a, b, c, pyropheophorbide and pheophytin may also be used, it is, however, not limited to these so long as the starting material is obtained from a photo-synthesized substance.

Table 1 illustrates data on Nuclear Magnetic Resonance absorption spectrum of a number of the inventive compounds, identified by substituents attached at the indicated sites on the following common basic molecular structure.

TABLE 1

| | ($\delta$ ppm) | | | | | | | | |
|---|---|---|---|---|---|---|---|---|---|
| | I | II | III | V | VI | VII | VIII | IX | X |
| Mw | 592 | 610 | 612 | 606 | 636 | 795 | 622 | 739 | 1182 |
| $\alpha$-H | 9.05 | 8.85 | 8.70 | 9.16 | 9.00 | 9.07 | 9.02 | 9.08 | 9.12 |
| $\beta$-H | 9.22 | 9.25 | 9.00 | 9.36 | 9.31 | 9.30 | 9.29 | 9.32 | 9.19 |
| $\delta$-H | 8.43 | 8.29 | 8.32 | 8.53 | 8.42 | 8.50 | 8.43 | 8.48 | 8.40 |
| 1-$CH_3$ | 3.26 | 3.25 | 3.15 | 3.30 | 3.22 | 3.25 | 3.38 | 3.26 | 3.37 |
| 2-CH=$CH_2$ | 7.72 | — | — | 7.83 | 7.70 | 7.73 | 7.71 | 7.72 | 7.80 |
|  | 6.05 | — | — | 6.15 | 6.10 | 6.10 | 6.10 | 6.10 | 6.15 |
|  | 5.95 | — | — | 6.06 | 5.93 | 5.98 | 6.01 | 5.96 | 5.99 |
| 3-$CH_3$ | 3.00 | 3.06 | 3.00 | 3.04 | 2.95 | 2.99 | 3.17 | 2.98 | 3.14 |
| 4b-$CH_3$ | 1.62 | 1.63 | 1.68 | 1.60 | 1.53 | 1.58 | 1.66 | 1.58 | 1.61 |
| 5-$CH_3$ | 3.57 | 3.43 | 3.22 | 3.60 | 3.52 | 3.52 | 3.62 | 3.52 | 3.59 |
| 7-H | 4.13 | 4.2 | 4.1 | 4.16 | 4.2 | 4.4 | 4.2 | 4.3 | 4.2 |
| 7a, b-$CH_2CH_2$— | 2~3 | 2~3 | 2~3 | 2~3 | 2~3 | 2~3 | 2~3 | 2~3 | 2~3 |
| 7c-$CH_3$ | — | — | — | 3.56 | 3.60 | 3.61 | — | 3.60 | — |
| 8-H | 4.40 | 4.7 | 4.4 | 4.44 | 4.5 | 4.55 | 4.4 | 4.53 | 4.43 |
| 8-$CH_3$ | 1.86 | 1.90 | 1.71 | 1.81 | 1.80 | 1.84 | 1.85 | 1.82 | 1.85 |
| 9-H | — | — | 6.69 | — | — | — | — | — | — |
| 10-H | 6.17 | 6.11 | 6.13 | 6.25 | 6.21 | 6.13 | 6.22 | 6.15 | 6.24 |
| 10b-$CH_3$ | 3.85 | 3.88 | 3.42 | 3.88 | — | — | — | — | — |
| 10b-$CH_2CH_2$— | — | — | — | — | 3.93 | — | 4.15 | — | — |
| 10b-$CH_2$— | — | — | — | — | — | — | — | — | 4.2 |
| 10b-$OBu^t$ | — | — | — | — | — | 1.40 | — | — | — |
| 10b-⟨C₆H₅⟩$CH_2$— | — | — | — | — | — | 7.2 | — | 7.2 | — |

As mentioned above, the present invention utilizes as the starting material photo-synthesized substances which are inexpensive and in stable supply. The reaction procedures involve extremely simple operations which can be conducted in a short period of time to achieve isolation and synthesis. The inventive compounds have physiological activities which are unique to phorbine related compounds and can be used per se as medical preparations, or offer unlimited possibilities as intermediates for manufacturing other medicine components. Unlike porphines derived from hemoglobin, they can be mass produced at higher purity and thus are extremely useful.

The preparation of the inventive compounds and their pharmacological effects will now be described by way of examples. Where sodium salts of such compounds are specified, they can be replaced by potassium and the like.

EXAMPLE 1

Laser Irradiation on a Removed Organ (in vitro)

(a) N₂ Pulsed Laser Spectro Fluorometry

Golden hamsters (5 per each group) 14-21 days after transplantation of nitrosoamine-induced cancer cells of the pancreas were administered 5 mg each of sodium 2-desethenyl-2-(1-hydroxyethyl)pheophorbide (sodium salt of II), sodium 2-desethynyl-2-(1-hydroxyethyl)-9-desoxo-9-hydroxy pheophorbide (sodium salt III), sodium 2-desethenyl-2-1(1-acetyloxyethyl)-9-desoxo-9-acetyloxy pheophorbide (sodium salt of IV), sodium ethylene glycol mono-10b pheophorbate (sodium salt of VIII), disodium ethylene glycol di-10b-pheophorbate (sodium salt of X) and sodium N-phenylalanine 10-b-methylpheophorbidamide (sodium salt of IX) respectively diluted with physiological saline (1 ml). Cancer cells and other organs were removed, irradiated with $N_2$-pulsed laser ($N_2$, 337 nm, 2 ns 400–1000 nm) to measure $N_2$ pulsed laser spectro fluorometry. Using the NADH peak wavelength of 470 nm as the reference, wavelengths in the range of from 600–900 nm were studied.

FIG. 1 shows that these products showed marked accumulation in cancer cells 24 hours after administration, but left no trace in other non-cancerous cells.

Similar tests were conducted on other compounds of the invention and the results are shown in Table 2 appearing hereafter. Various organs were removed 24 hours after administration and their $N_2$ pulsed laser spectro fluorometry was measured. Using the NADH peak wavelength of 470 nm as the reference, the wavelengths were calculated and shown in Table 2.

As is evident from the results above, these phorbine related compounds have a marked selective affinity to cancer cells.

(b) Biochemical Luminescence by Single Photon Counter

Leukemic Molt 4 cell ($1 \times 10^7$ cells) was added with physiological saline containing sodium 2-desethenyl-2-(1-hydroxyethyl)photophorbide (sodium salt of II) in respective concentractions of 25 μg/2 ml, 50 μg/2 ml, and 100 μg/2 ml, and then incubated (37° C., 24 hours). The several samples of incubated cells each were irradiated with laser (He-He gas, 630 nm, 10 min, 20 mW) to determine the generation of biochemiluminescence by the single photoncounter system by measuring biochemiluminescence. The intensity of biochemiluminescence by the single photoncounter system substantially corresponds to the degree of destruction of the cancer cells. Therefore, by observing generation of biochemiluminescence by the single photoncounter system, destruction of cancer cells may be predicted.

TABLE 2

| (Sodium compounds) | |
|---|---|
| Comparison | |
| Pheophorbide (I) | 0.78 |
| 9-Desoxo-9-hydroxy-pheophorbide | 0.93 |
| Pyropheophorbide | 0.25 |
| Application | |
| 9-Desoxo-9-hydroxy-pheophorbide + ethylene glycol mono-10b-methylpheophorbate (VI) | 2.00 |
| 9-Desoxo-9-hydroxy-pyropheophorbide | 0.98 |
| 9-Desoxo-9-hydroxy-pheophorbide C | 0.32 |
| 9-Desoxo-9-acetyloxy-pheophorbide | 0.89 |
| N—Phenylalanine 10b-methylpheophorbidamide (IX) | 0.75 |
| 2-Desethenyl-2-(1-acetyloxyethyl)-pheophorbide | 0.38 |
| 2-Desethenyl-2-(1-hydroxyethyl)-9-desoxo-9-hydroxy-pheophorbide (III) | 3.13 |
| 2-Desethenyl-2-(1-acetyloxyethyl)-9-desoxo-9-acetyloxypheophorbide (IV) | 0.48 |
| 2-Desethenyl-2-(1-acetyloxyethyl)-9-desoxo-9-hydroxy-pheophorbide | 0.95 |
| N—phenylalanine 10b-9-desoxo-9-hydroxy-methylpheophorbidamide | 0.73 |
| Ethylene glycol di-10b-pheophorbate (X) | 2.78 |
| Ethylene glycol di-10b-9-desoxo-9-hydroxypheophorbate | 2.50 |
| Ethylene glycol mono-10b-pheophorbate (VIII) | 1.72 |
| Monoacetylethylene glycol mono-10b-pheophorbate | 1.30 |
| Ethylene glycol mono-10b-9-desoxo-9-hydroxy-pheophorbate | 2.10 |
| Monoacetylethylene glycol mono-10b-9-desoxo-9-acetyloxy-pheophorbate | 0.85 |
| Monoacetylethylene glycol mono-10b-9-desoxo-9-hydroxy-pheophorbate | 1.20 |
| 2-Desethenyl-2-(1-hydroxyethyl)-pheophorbide (II) | 1.90 |
| Ethylene glycol di-10b-2-desethenyl-2-(1-hydroxyethyl)-pheophorbate | 2.50 |
| Ethylene glycol di-10b-2-desethenyl-2-(1-hydroxyethyl)-9-desoxo-9-hydroxy-pheophorbate | 1.80 |

Figure 2:
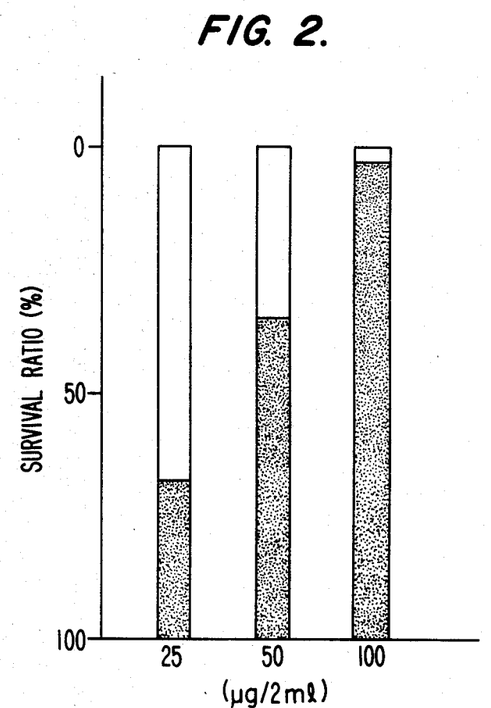

FIG. 2 shows the degree of biochemiluminescence and the destruction of cancer cells after laser irradiation. These results indicate that when 100 μg/2 ml of this test compound was used, more than 95% of the cancer cells were destroyed.

As is evident from the results shown in FIG. 2, the present compounds are highly photo-sensitive and display a marked destructive effect on cancer cells.

EXAMPLE 2

One gram of pheophorbide (I) was dissolved in a 25 g solution of hydrobromic acid in acetic acid and reacted for 15 hours with stirring. After the reaction was complete, 50 ml of water was added while stirring and the reaction mixture then neutralized by adding 20 ml of 33% NaOH aqueous solution, whereby crystals of 2-desethenyl-2-(1-hydroxyethyl)-pheophorbide (II) were precipitated. Crystals were then collected, washed with water and dried (yield: 1 g). The yield was 97%.

The resultant product II was dissolved in acetone, mixed with 5% $Na_2CO_3$ aqueous solution for neutralization to obtain sodium 2-desethenyl-2-(1-hydroxyethyl)-pheophorbide (II). The yield was 98%.

EXAMPLE 3

One gram of II was dissolved in 6 ml of pyridine and 30 ml of methanol, dropped with 5% NaBH$_4$ aqueous solution with stirring and reacted. After the reaction was completed, a 5% aqueous solution of citric acid was added to separate excess NaBH$_4$. Water was then added to the reaction product and crystals of 2-desethenyl-2-(1-hydroxyethyl)-9-desoxo-9-hydroxy-pheophorbide (III) were precipitated. Crystals were collected, washed with water and dried (yield 1 g). The yield was 98%.

EXAMPLE 4

One gram of III was acetylated using a solution of acetic anhydride in pyridine by the conventional method to obtain the diacetylate (IV) of III (yield 1.1 g). The yield was 99%.

EXAMPLE 5

One gram of methyl pheophorbide (V) and 2 g of ethylene glycol were dissolved in 20 ml of DMF and reacted for 2 hours under heating and stirring. After the reaction was completed, water was added to precipitate crystals of ethylene glycol mono-10b-methyl pheophorbate (VI). Crystals were collected, washed with water and dried (yield 0.7 g). The yield was 70%.

The product VI (0.7 g) thus obtained was dissolved in 10 ml of 50% H$_2$SO$_4$ and reacted for 1 hour at room temperature under stirring. After the reaction was completed, water was added to precipitate crystals of ethylene glycol mono-10b-pheophorbate (VIII). Crystals were collected, washed with water and dried (yield 0.65 g). The yield was 95%.

EXAMPLE 6

One gram of V and 2 g of phenylalanine t-butyl ester were dissolved in 30 ml of xylene and reacted for 2 hours under heating and stirring. After the reaction was completed, the reaction solution was subjected to column chromatography [silicic acid column, n-hexane:ethyl acetate (3:1)] to obtain N-phenylalanine-tubutyl ester 10b-methylpheophorbidamide (VII) (yield 0.9 g). The yield was 68%.

The resultant product VII (0.9 g) was dissolved in 10 ml of trifluoro acetic acid and reacted for 2 hours at room temperature under stirring. After the reaction was completed, water was added to precipitate crystals of N-phenylalanine 10-b-methylpheophorbidamide (IX). Crystals were collected, washed with water and dried (yield 0.8 g). The yield was 95%.

EXAMPLE 7

One gram of VIII and 1 g of I were dissolved in 20 ml of DMF and reacted for 2 hours under heating and stirring. After the reaction was completed, water was added to precipitate crystals of ethylene glycol di-10b-pheophorbate (X). Crystals were collected, washed with water and dried (yield 1.5 g). The yield was 80%.

What is claimed is:
1. A pheophorbide derivative and its alkaline salts having the general formula (A):

wherein
$R_1$ represents —CH=CH$_2$, —CH(OH)CH$_3$, —CH(OCH$_2$CH$_2$OH)CH$_3$ or —CH(OCOCH$_3$)CH$_3$
$R_2$ represents —CH$_3$, —CHO or —CH$_2$OH
$R_3$ represents =O, —OH or —OCOCH$_3$
$R_4$ represents —H, —COOCH$_3$, —COOCH$_2$C-H$_2$OH, —COOCH$_2$CH$_2$OCOCH$_3$, or a —CONH— containing residue of an amino acid and
$R_5$ represents —COOH, —COONa or —COOCH$_3$;
provided that $R_2$ is not —CH$_3$ or —CH$_2$OH when $R_3$ is —OH or —OCOCH$_3$, $R_5$ is neither COOH nor COON$_a$ when $R_4$ is —COOCH$_3$ and $R_3$ is=O, —OH, or —COOCH$_3$, and $R_5$ is neither —COOH nor—COOCH$_3$ when $R_4$ is COOCH$_3$ or —H; and dimeric pheophorbide derivatives and alkaline salts thereof represented by the general formula (B):

where $R_1$ through $R_5$ represent residual radicals identical to those in the general formula (A) provided that $R_5$ is not carboxy methyl.

* * * * *

UNITED STATES PATENT AND TRADEMARK OFFICE
CERTIFICATE OF CORRECTION

PATENT NO. : 4,709,022

DATED : November 24, 1987

INVENTOR(S) : Isao Sakata et al

It is certified that error appears in the above-identified patent and that said Letters Patent is hereby corrected as shown below:

In the Heading:

The following should be inserted:

-- [73] Assignee: Toyo Hakka Kogyo Kabushiki Kaisha, Okayama, Japan --.

Signed and Sealed this

Twenty-ninth Day of March, 1988

Attest:

DONALD J. QUIGG

Attesting Officer     Commissioner of Patents and Trademarks